United States Patent

Reetz et al.

[11] Patent Number: 5,962,718
[45] Date of Patent: Oct. 5, 1999

[54] ZIRCONOCENES AND HAFNOCENES WITH BORON-SUBSTITUTED CYCLOPENTADIENYL-LIGANDS AND THE METHOD OF PRODUCING THEM

[75] Inventors: Manfred T. Reetz, Mülheim an der Ruhr; Hanno Brümmer, Düsseldorf; Christian Psiorz, Essen; Marc Willuhn, Mülheim an der Ruhr, all of Germany

[73] Assignee: Studiengesellschaft Kohle MbH, Mulheim An Der Ruhr, Germany

[21] Appl. No.: 09/051,609
[22] PCT Filed: Oct. 22, 1996
[86] PCT No.: PCT/EP96/04572
  § 371 Date: Apr. 16, 1998
  § 102(e) Date: Apr. 16, 1998
[87] PCT Pub. No.: WO97/15581
  PCT Pub. Date: May 1, 1997

[30] Foreign Application Priority Data

Oct. 25, 1995 [DE] Germany .............. 195 39 650

[51] Int. Cl.$^6$ ............................................. C07F 7/00
[52] U.S. Cl. ................. 556/51; 556/7; 556/11; 556/1
[58] Field of Search ................. 556/51, 7, 11, 556/1

[56] References Cited

U.S. PATENT DOCUMENTS

| | | | |
|---|---|---|---|
| 5,169,818 | 12/1992 | Antberg et al. | 556/51 |
| 5,262,498 | 11/1993 | Antberg et al. | 556/51 |
| 5,468,889 | 11/1995 | Srebnik et al. | 556/7 |

OTHER PUBLICATIONS

Bochmann et al; J. Chem. Soc., Chem. Commun; 1995; p. 2081.

*Primary Examiner*—Louise N. Leary
*Attorney, Agent, or Firm*—Sprung Kramer Schaefer & Briscoe

[57] ABSTRACT

Zirconocenes and hafnocenes with borylated cyclopentadienyl ligands and methods for the preparation thereof.

16 Claims, No Drawings

ZIRCONOCENES AND HAFNOCENES WITH BORON-SUBSTITUTED CYCLOPENTADIENYL-LIGANDS AND THE METHOD OF PRODUCING THEM

The present invention relates to a generally applicable synthetic method for the preparation of as yet unknown zirconocenes and hafnocenes bearing a boron-containing substituent directly on the cyclopentadienyl ligand. These compounds will be used in a novel application in the polymerization of olefins with cocatalysis by aluminum alkyl compounds.

A wide variety of metallocene-based catalyst systems is known from the literature. They all share the necessity of a cocatalyst which converts the metallocene to an active form capable of polymerizing olefins. According to a generally accepted idea, a zirconium cation is generated thereby.

PRIOR ART

Metallocenes are usually activated as dichloride compounds with a large excess (1000–10,000:1) of methylalumoxane (MAO) (V. K. Gupta, S. Satish, I. S. Bhardwaj, J. M. S.—Rev. Macromol. Chem. Phys. 1994, C34(3), 439–514). MAO-free systems are based on the use of dialkylmetallocenes with "cationizing reagents". Good polymerization properties are only exhibited by "ligand-free" systems (R. F. Jordan, Adv. Organomet. Chem. 1991, 32, 325). Common cationizing reagents are ammonium compounds (H. W. Turner, Eur. Pat. Appl. 277004), acidic carboranes (D. J. Cowther, N. C. Baenziger, R. F. Jordan, J. Am. Chem. Soc. 1991, 113, 1455), boron Lewis acids (A. R. Siedle, R. A. Newmark, W. M. Lamanna, J. C. Huffman, Organometallics 1993, 12, 1491; X. Yang, C. L. Stern, T. J. Marks, J. Am. Chem. Soc. 1991, 113, 3623) or tritylium salts (M. Bochmann, S. J. Lancaster, J. Organomet. Chem. 1992, 434, C1).

Drawbacks of these methods are the often insufficient stabilities of the metallocene alkyl compounds and of the mixtures with cationizing reagents. In addition, the dependence of polymerization activity on the amount of cationizing reagent and preactivation time is a complex relationship which is not understood in detail.

One possibility of circumventing the synthesis is an in situ alkylation method (W.-M. Tsai, M. D. Rausch, J. C. W. Chien, Appl. Organomet. Chem. 1993, 7, 71). However, this method causes an effective polymerization catalysis only if the order of additions and the preactivation time are precisely observed.

Metallocenes with borylated cyclopentadienyl ligands represent potential polymerization catalysts since the attachment of a strong Lewis acid should enable the subsequently performed formation of a zwitterionic compound through the conjugated π system of the ligand.

Borylated zirconocenes and hafnocenes are not described in the literature. They cannot be successfully synthesized by common methods of metallocene synthesis (D. J. Cardin, M. F. Lappert, C. L. Raston, Chemistry of Organo-Zirconium and -Hafnium Compounds, Ellis Horwood Ltd., Chichester, 1986) since the treatment of borylated cyclopentadienes with bases or metalization reagents will result in a cleavage of the B—C bond.

The transfer of silylated cyclopentadienyl ligands to zirconium is known (K. W. Krebs, H. Engelhard, G. E. Nischk (Bayer AG), Ger. Offen. 1,959,322, 1971; Chem. Abstr. 1971, 75, P88768P, and C. Winter, X.-X. Zhou, D. A. Dobbs, M. J. Heeg, Organometallics 1991, 10, 210). By the method described therein, the corresponding borylated zirconocenes and hafnocenes can be synthesized from precursors which are both borylated and silylated.

A systematic approach to the borylated and silylated cyclopentadienes does not exist. Alkoxyboranes or amine adducts of alkylboranes can be introduced via metallated precursors (B. M. Mikhailov, T. K. Baryshnikova, V. S. Bogdanov, Dokl. Akad. Nauk SSSR 1972, 202, 358, and H. Grundke, P. I. Paetzold, Chem. Ber. 1971, 104, 1136). Haloboranes are obtainable through Si—B exchange, and alkoxyboranes are obtainable through Sn—B exchange (P. Jutzi, A. Seufert, J. Organomet. Chem. 1979, 169, 327).

No generally applicable method exists for the synthesis of alkylboranes.

The above results have now been extended to a generally applicable method for the synthesis of zirconocenes and hafnocenes.

Starting from cyclopentadienes and substituted cyclopentadienes (see below) having an Si and an Sn substituent, reaction with various haloboranes bearing further residues yields an Si—B cyclopentadiene which is reacted with halides of zirconium and hafnium to give the corresponding metallocenes.

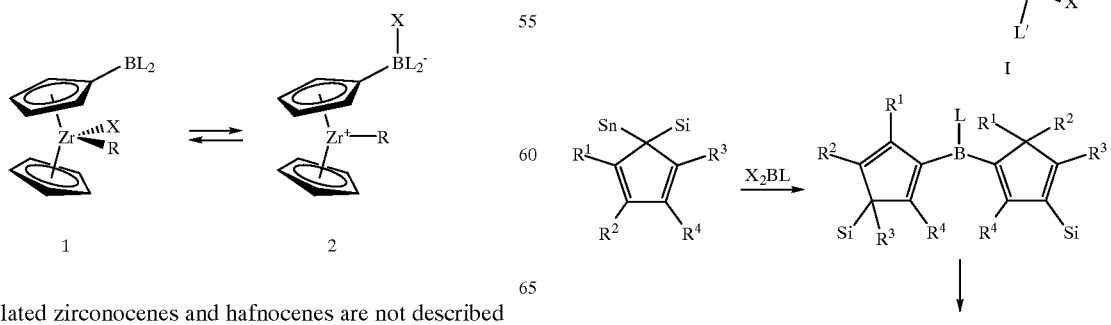

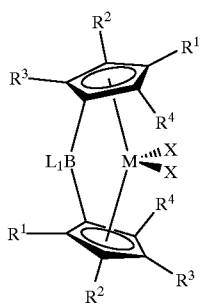

Metallocenes having the following general structures can be obtained:

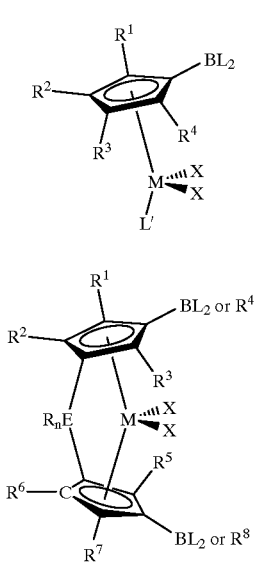

One of the cyclopentadienyl ligands may be unsubstituted ($R^1$, $R^2$, $R^3$, $R^5$, $R^6$, $R^7$=H; $R^4$, $R^8$=$BL_2$) or substituted cyclopentadienyls. Examples of substituents of the substituted cyclopentadienyls include $R_1$, $R^2$, $R^3$, $R^5$, $R^6$, $R^7$=methyl, ethyl, allyl, phenyl, aryl, benzyl residues and heteroatoms, such as halogens (F, Cl, Br, I), silicon, germanium. The cyclopentadienyl ligands may also be anellated cyclopentadienyl ligands, such as indenyl, tetrahydroindenyl, which may again bear substituents, such as alkyl, aryl, benzyl residues or heteroatoms, such as halogens (F, Cl, Br, I), silicon and germanium.

The other cyclopentadienyl ligand may be the same as the first, but it may also be boron-free and bear the same or different substituents, as mentioned above. L' may be another cyclopentadienyl ligand like the first, i.e. bear the same or different substituents, but it may also be boron-free. L' may be equal to X=halogen.

The bridge $R_nE$ may be bridges E, 2E or 3E with n=1–2, composed of the same or different constituents containing a group with a IVth main group element (E=C, Si, Ge; R=H, alkyl, aryl, benzyl), such as $CH_2$, $CR_2$, $SiR_2$ or $GeR_2$.

If such a bridge is present, $R^1$ to $R^4$ may be different from $R^5$ to $R^8$.

However, it may also contain boron [E=B, n=1, R=H, alkyl, aryl, benzyl, fluorinated alkyl or aryl, alkoxy, OH, halogens (F, Cl, Br, I)] alone, in combination with above mentioned bridge constituents or with a VIth main group element, such as oxygen or sulfur. If the bridge consists of only one B ($R_nE$=$L_1B$), $R^4$ and $R^8$ may also be methyl, ethyl, allyl, phenyl, aryl, benzyl residues and heteroatoms, such as halogens (F, Cl, Br, I), silicon, germanium. If the bridge consists of only one boron, $R^1$ to $R^4$ are the same as $R^5$ to $R^8$.

The substituent L at the boron of the cyclopentadienyl ligand or at the boron of the bridge may be alkyl, aryl, benzyl, fluorinated alkyl or aryl, halogens (F, Cl, Br, I), OH, alkoxy, wherein these residues may be part of a cycle.

The substituents X at the transition metal may be a halogen or nitrogen.

The same metallocene complexes are obtainable by an alternative synthetic route. Thus, boron-substituted cyclopentadiene compounds are deprotonated with weakly nucleophilic bases, such as lithium bis(trimethylsilyl)amide, and then converted to the corresponding metallocenes by a transmetallation. Although the deprotonation of boron-substituted cyclopentadiene compounds with sterically demanding bases is known (G. E. Herberich, A. Fischer, Organometallics 1996, 15, 58–67), neither was lithium bis(trimethylsilyl)amide used as the base, nor was the deprotonation examined with bridged ligand systems.

With the alternative method described herein, the corresponding borylated zirconocenes and hafnocenes can be synthesized from all borylated precursors. In these cases, the precursors need not necessarily be silylated. In the case of zirconocenes and hafnocenes comprising a one-membered boron bridge, complexes are also obtainable which possess differently substituted cyclopentadienyl rings.

Zirconocenes and hafnocenes with other bridges can also be obtained by a mild thermolysis of bisborylated zirconocene and hafnocene derivatives with alkoxy residues at the boron:

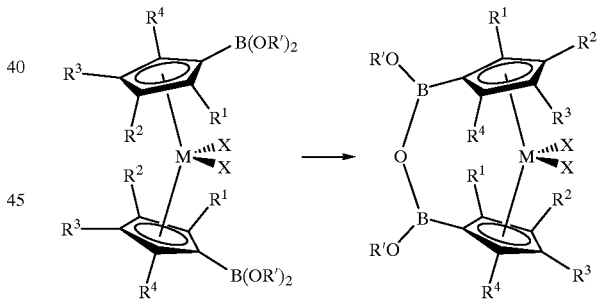

The residues R' may be any alkyl or aryl groups. X, M and $R^1$ to $R^4$ are as defined above.

The thus preparable zirconocenes and hafnocenes can be used as a catalyst component in olefin polymerization, wherein an activity can be measured which is increased by a factor of up to 10 as compared with the parental compound $Cp_2ZrCl_2$ of the zirconocenes.

EXAMPLES

1. Unbridged Zirconocene with Two Alkyl Residues at the Boron, Both Cyclopentadienyl Ligands Being Boron-substituted Preparation of diethyl (trimethylsilylcyclopentadienyl)borane To 5.44 g (18.1 mmol) of colorless neat trimethyl (trimethylsilylcyclopentadienyl)tin is added 1.89 g (2.28 ml, 18.1 mmol) of colorless chlorodiethylborane at once at room temperature. An intense yellow color immediately appears. The mixture is stirred for 2 h and then subjected to fractional distillation. At a bath temperature of 60° C., the major part of the chlorotrimethylstannane can be separated off as the first fraction.

Yield: 3.34 g (16.2 mmol, 90%), pale yellow liquid, b.p. 42° C./0.4 mbar.

Main Isomer $^1$H NMR (200.13 MHz, CDCl$_3$): δ=6.55 (m, br, 4H, Cp-H), 1.40 (q, $^3$J=7.5 Hz, 4H, CH$_2$—CH$_3$), 1.00 (t, $^3$J=7.5 Hz, 6H, CH$_3$—CH$_2$), −0.06 [s, 9H, (CH$_3$)$_3$Si].

Minor Isomer $^1$H NMR (200.13 MHz, CDCl$_3$): δ=7.52 (m, 1H, Cp-H), 7.44 (m, 1H, Cp-H, 7.06 (m, 1H, Cp-H), 6.95 (m, 1H, Cp-H), 3.28 (m, 1H, allyl-Cp-H), 1.40 (q, $^3$J=7.5 Hz, 4H, CH$_2$—CH$_3$) 1.00 (t, $^3$J=7.5 Hz, 6H, CH$_3$—CH$_2$), 0.18 [s, 9H, (CH$_3$)$_3$Si].

All Isomers $^{13}$C NMR (50.32 MHz, CDCl$_3$): δ158.2, 151.0, 150.7, 147.2, 141.6 (vinyl-Cp-C), 131 [br, Cp-C(BR$_2$)], 47.7, 46.3 (allyl-Cp-C), 16 (br, CH$_2$), 8.3, 8.2 (CH$_3$), 1.5, −1.9, −2.13 [(CH$_3$)$_3$Si].

$^{11}$B NMR (64.21 MHz, CDCl$_3$): δ=73.

MS (EI, 70 eV): m/z (%)=206 (6) [M$^+$].

Preparation of bis[η$^5$-diethylborylcyclopentadienyl] dichlorozirconium(IV)

To a suspension of 0.970 g (4.16 mmol) of zirconium tetrachloride in 40 ml of toluene is added 1.89 g (2.34 ml, 9.16 mmol) of diethyl(trimethylsilylcyclopentadienyl) borane dropwise at room temperature. The mixture is heated to 60° C.; after 2 h, an almost clear grey-yellow solution has formed. After cooling to room temperature and stirring over night, the mixture is filtered, highly concentrated and crystallized at −30° C. The precipitated crystalline colorless solid is separated, washed with cold hexane and dried in vacuo. A further crop can be obtained from the mother liquor by the addition of pentane and renewed crystallization at −30° C.

Yield: 1.59 g (3.70 mmol, 89%) of colorless shining scales.

$^1$H NMR (400.14 MHz, [D$_6$]benzene): δ=6.64 (ps-t, 4H, α-Cp-H), 6.00 (ps-t, 4H, β-Cp-H), 1.56 (q, $^3$J=7.5 Hz, CH$_2$—CH$_3$) , 1.10 (t, $^3$J=7.5 Hz, CH$_3$—CH$_2$)

$^{13}$C NMR (50.32 MHz, [D$_6$]benzene): δ=124.1 (α-Cp-C), 118.1 (β-Cp-C), 18 (br, CH$_2$—B), 8.7 (CH$_3$).

$^{11}$B NMR (64.21 MHz, [D$_6$]benzene): δ=71.

MS (70 eV, evaporation temperature 100° C.) : m/z (%)=397 (100) [M$^+$- C$_2$H$_5$]

2. Unbridged Zirconocene with Alkyl Residues which are Part of a Ring System, Only One Cyclopentadienyl Ligand Being Boron-substituted Preparation of (3-trimethylsilylcyclopentadienyl)-3-methyl-2,3-dihydro-1-benzoborol To 3.88 g (3.30 ml, 12.9 mmol) of pale yellow trimethyl (trimethylsilylcyclopentadienyl)tin is rather quickly added 2.12 g (2.25 ml, 12.9 mmol) of (B-chloro)(3-methyl-2,3-dihydro)-1-benzoborol dropwise at room temperature. The mixture turns slightly yellow which is somewhat intensified after stirring at room temperature for 4 h. It is subsequently subjected to fractional distillation. At a bath temperature of 70° C. and a pressure of 1 mbar, the chlorotrimethylstannane formed can be quantitatively separated off as the first fraction.

Yield: 3.178 g (11.94 mmol, 93%), pale yellow liquid, b.p.: 35° C./10$^{-3}$ mbar.

$^1$H NMR (200.13 MHz, [D$_6$]benzene): δ=8.11 (m, 1H, H6, minor isomer), 8.07 (d, $^3$J$_{H6H5}$=7.2 Hz, 1H, H6), 7.88, 7.64 (both m, 1H, Cp-H), 7.36 (2 dd, $^3$J=7 Hz, H4/5), 7.21 (m, 1H, H3), 7.02, 6.98 (both m, 1H, Cp-H), 6.65 (br, 4H, CpH, main isomer), 3.52, 3.41 (both m, 1H, allyl-Cp-H, minor isomers), 3.25 (dq, $^3$J$_{H1aH2}$=$^3$J$_{H2Me-H}$=7.3 Hz, $^3$J$_{H1bH2}$=2.9 Hz, 1H, H2) 2.10 (m, 1H, H1a), 1.30 (dd, $^3$J$_{H1bH2}$=2.9 Hz, 1H, H1b), 1.28 (d, $^3$J=7.3 Hz, 3H, CH$_3$), 0.23, 0.21 [both s, 9H, (CH$_3$)$_3$Si, minor isomers], −0.13 [s, 9H, (CH$_3$)$_3$Si, main isomer].

$^{13}$C NMR (50.32 MHz, [D$_6$]benzene): δ=170.2 (s, C2a, minor isomer), 170.0 (s, C2a, main isomer), 159.2, 154.3, 152.5, 150.6, 143.1 (all Cp-C), 133.6, 132.9, 125.9, 125.0 (all Ph-C, C3–C6, main isomer), 133.3, 132.9, 125.1 (all Ph-C, C3–C6, minor isomer), 49.6 (allyl-Cp-C, main isomer), 48.1 (allyl-Cp-C, minor isomer), 39.8, 39.7 (both d, C2), 35, 34 (both br, C1), 24.0, 29.9 (both q, CH$_3$), −0.7, −1.0 [both (CH$_3$)Si, minor isomers], −1.1 [br, (CH$_3$)$_3$Si, main isomer].

$^{11}$B NMR (64.21 MHz, [D$_6$]benzene): δ=62.

MS (EI, 70 eV, evaporation temperature 35° C.) : m/z (%) 266 (16) [M$^+$].

Preparation of (η$^5$-(3-methyl-2,3-dihydrobenzoboroyl)cyclopentadienyl) (η$^5$-cyclopentadienyl)dichlorozirconium(IV)

To a suspension of 0.483 g (1.84 mmol) of (η$^5$-cyclopentadienyl)trichlorozirconium(IV) in 30 ml of toluene is added rather quickly 0.54 g (0.58 ml, 2.0 mmol) of (trimethylsilylcyclopentadienyl)-3-methyl-2,3-dihydro-1-benzoborol at room temperature. The mixture is heated to 60° C.; after 2 h, a clear grey-yellow solution has formed. After cooling and stirring over night, the mixture is concentrated to about 5 ml in vacuo, and 20 ml of hexane is added. A voluminous pale grey precipitate forms. The precipitation is completed at −30° C., the precipitate is separated and dried in vacuo.

Yield: 0.594 g, grey powder.

The solid still contains 10–20% of the bis(η$^5$-(3-methyl-2,3-dihydrobenzoboroyl)cyclopentadienyl) dichlorozirconium(IV). However, when recrystallized from a small amount of hot toluene, it completely crystallizes at room temperature together with some of the unsymmetrical zirconium compound. After further concentrating, the pure substance precipitates from the mother liquor at −78° C.

Yield: 0.226 g (0.269 mmol, 30%), off-white solid.

$^1$H NMR (200.13 MHz, [D$_6$]benzene) :δ=8.05 (td, $^3$j=7.3 Hz, 2H, H6), 7.33 (m, 1H, H3/4/5), 7.31 (m, 1H, H3/4/5), 7.20 (m, 1H, H3/4/5), 6.92 (m, 1H α-Cp-H), 6.88 (m, 1H, α-Cp-H), 6.21 (m, 2H, β-Cp-H), 5.91 (s, 5H, Cp-H, unsubst. Cp), 3.23 (dquint, $^3$J$_{H2H1a}$=$^3$J$_{H2CH3}$=7.0 Hz, $^3$J$_{H2H1b}$=3.0 Hz, 1H, H2), 2.12 (dd, J$_{H1aH1b}$=19.2 Hz, $^3$J$_{H1aH2}$=7.0 Hz, 1H, H1a), 1.37 (dd, $^2$J$_{H1bH1a}$=19.2 Hz, $^3$J$_{H1bH2}$=3.0 Hz, 1H, H1b), 1.27 (d, $^3$J =7.0 Hz, 3H, CH$_3$—CH)

$^{13}$C NMR (50.32 MHz, [D$_6$]benzene): δ=171.2 (s, C2a), 133.7, 133.4, 127.1 (all d, Ph-C, C3–C6), 126.2, 126.2 (both d, α-Cp-C), 125.4 (d, Ph-C), 120.1, 120.0 (both d, β-Cp-C), 116.1 (d, 5C, unsubst. Cp), 39.7 (d, C2), 34 (br, C1), 23.7 (CH$_3$).

$^{11}$B NMR (64.21 MHz, [D$_6$]benzene): δ=68.

MS (EI, 70 eV, evaporation temperature 95° C.); m/z (%): 418 (16) [M$^+$].

3. Unbridged Zirconocene with Alkoxy Residues which are part of a Ring System, only one Cyclopentadienyl Ligand being Boron-substituted

Preparation of trimethylsilylcyclopentadienyl-2,3-dioxabenzoborol

To 3.15 g (20.4 mmol) of solid, finely ground B-chloro-2,3-dioxabenzoborol is added 6.10 g (20.4 mm =l) of trimethyl-(trimethylsilylcyclopentadienyl) tin dropwise at room temperature. A clear solution forms which turns yellow at room temperature within 2 h.

In the distillative processing of the reaction mixture, the chlorotrimethylstannane formed is first quantitatively sublimated off at p>1 mbar and 50° C. bath temperature.

After distillation, the solid which congeals at room temperature can be recrystallized from hexane to yield short colorless needles.

Yield: 4.24 g (16.6 mmol, 81%), colorless solid, b.p. 95° C./ $2 \cdot 10^{-3}$ mbar.

$^1$H NMR (400.14 MHz, [D$_6$]benzene): δ=7.76 (m, 1H), 7.20, 7.17, 6.93, 6.89 (all dd, $J_{AX}$=6 Hz, $J_{AX'}$=2 Hz, $J_{XX'}$=6 Hz, Ph-H), 6.7 (m, br, 4H, Cp-H, main isomer), 3.42, 3.36 (both m, 1H, allyl-Cp-H), 0.25, 0.21 [both s, 9H, (CH$_3$)$_3$Si vinylic], 0.01 [s, 9H, (CH$_3$)$_3$Si allylic, main isomer].

$^{13}$C NMR (100.63 MHz, [D$_6$]benzene): δ=157.9, 153.3, 150.7, 149.6, 142.4 (all Cp-C), 149.0 (ipso-Ph-C), 122.8 (ortho-Ph-C), 112.5 (meta-Ph-C), 48.5, 47.2 (both allyl-Cp-C), 1.4, −0.9 [both (CH$_3$)$_3$Si vinylic], −1.7 [(CH$_3$)$_3$Si allylic].

$^{11}$B NMR (64.21 MHz, [D$_6$]benzene): δ=31.

MS (EI, 70 eV, evaporation temperature 20° C.): m/z (%) =256 (25) [M$^+$].

Preparation of (η$^5$-2,3-dioxabenzoboroylcyclopentadienyl) (η$^5$-cyclopentadienyl)dichlorozirconium(IV)

To a suspension of 0.204 g (0.777 mmol) of (η$^5$-cyclopentadienyl)trichlorozirconium(IV) in 20 ml of toluene is added a solution of 0.221 g (0.863 mmol) of (trimethylsilylcyclopentadienyl)-2,3-dioxabenzoborol in 10 ml of toluene at once at room temperature. The mixture is heated to 80° C., stirred for 6 h, diluted to a total volume of 60 ml, and stirred for another 2 h. A clear, slightly grey solution forms which is allowed to cool to room temperature, filtered and highly concentrated. After cooling to −30° C., a grey solid precipitates after 1 day which, after separating and drying, can be recrystallized from toluene.

Yield: 0.234 g (0.570 mmol, 73%), light-grey solid.

$^1$H NMR (400.14 MHz, [D$_6$]benzene): δ=7.06 (dd, $J_{AX}$=6 Hz, $J_{AX'}$=$J_{A'X}$=2 Hz, 2H, α-Ph-H), 6.82 (ps-t, 2H, α-Cp-H), 6.78 (dd, $J_{XX'}$=6 Hz, $J_{AX'}$=$J_{A'X}$=2 Hz, 2H, β-Ph-H), 6.00 (ps-t, 2H, β-Cp-H), 5.02 (s, 5H, unsubst. Cp-H).

$^{13}$C NMR (100.63 MHz, [D$_6$]benzene): δ=148.6 (ipso-Ph-C), 124.0, 123.2, 119.0, 116.3, 112.9 (all Cp-C or Ph-C).

$^{11}$B NMR (64.21 MHz, [D6] benzene): δ=29.

MS (70 eV, evaporation temperature 100° C.): m/z (%) =408 (34) [M$^+$ ].

4. Unbridged Zirconocene with Perfluorinated Phenyl Substituents at the Boron, both Cyclopentadienyl Ligands being Boron-Substituted

Preparation of bis(pentafluorophenyl) (trimethylsilylcyclopentadienyl) borane To 3.6 3 g (9.54 mmol) of solid, finely ground chlorobis (pentafluorophenyl)borane is added 2.87 g (2.38 ml, 9.54 mmol) of trimethyl (trimethylsilylcyclopentadienyl) tin pre-cooled to −20° C. at once at −20° C. with vigorous stirring. A yellow paste forms immediately and increasingly solidifies. The mixture is allowed to reach room temperature whereupon the paste at first softens and then suddenly congeals to a solid cake. Under oil-pump vacuum, the major part of chlorotrimethylstannane formed is removed within 24 h. The tan-colored residue is recrystallized from a small amount of hexane, and the tan-colored residue is again dried under oil-pump vacuum for 24 h. This process may be repeated several times, but never will all of the chlorotrimethyltin be removed. Also, the bis(pentafluorophenyl)(3-trimethylsilylcyclopentadienyl)borane is still contaminated by higher molecular weight compounds. Due to its temperature sensitivity, distillation is not possible.

Yield: about 80–90% (NMR).

$^1$H NMR (200.13 MHz, [D$_6$]benzene): δ=7.52 (m, br, 1H, Cp-H), 7.19 (m, br, 2H, Cp-H), 6.81 (m, br, 1H, Cp-H), 6.48 (m, br, 4H, Cp-H, main isomer), 4.6 (m, br, 2H), 3.41 (m, 1H, allyl-Cp-H), 0.05 [s, 9H, (CH$_3$)$_3$Si, minor isomers], −0.32 [s, 9H, (CH$_3$)$_3$Si, main isomer].

$^{13}$C NMR (50.32 MHz, [D$_6$]benzene): δ=156 (m, br), 150 (m, br), 141 (m, br, all Ar-C), 133.7, 131.7, 130.0, 126.2 (all Cp-C), −0.9, −1.1, −1.4, −2.3 [all (CH$_3$)$_3$Si].

$^{11}$B NMR (64.21 MHz, [D$_6$]benzene): δ=53.

MS (EI, 70 eV, evaporation temperature 60° C.): m/z (%) =482 (5) [M$^+$].

Preparation of bis [η$^5$-bis(pentafluorophenyl) borylcyclopentadienyl]dichlorozirconium(IV)

To a suspension of 0.456 g (1.96 mmol) of zirconium tetrachloride in 40 ml of toluene is added a solution of 2.12 g (4.40 mmol) of bis(pentafluorophenyl) (trimethylsilylcyclopentadienyl)borane in 20 ml of toluene at once at room temperature. The mixture is heated at 40° C. for 3 h to give an almost clear tan-colored solution. The solution is filtered, and the solvent removed in vacuo at room temperature. A brown oil remains, and sometimes spontaneous crystallization occurs shortly before dryness is reached. The oil is digested in a small amount of hexane until a yellow voluminous precipitate forms. The mixture is filtered, and the yellow residue is sequentially digested with a small amount of hot hexane, allowed to cool to room temperature and filtered until a colorless powder forms. The latter is dissolved in as small as possible an amount of hot toluene (about 60–80° C.), the double amount of hot hexane is added, and the solution is allowed to cool. A microcrystalline colorless precipitate forms. The crystallization is completed at 4, −30 and −78° C. After removing the mixture of solvents, a snow-white powder remains. All mother liquors which contain toluene are evaporated to dryness in vacuo, and further crops of product are isolated and purified as described above.

Yield: 1.23 g (64%), colorless solid.

The generally determined yield over two steps, proceeding from chlorobis(pentafluorophenyl)borane, is up to 57%:

$^1$H NMR (400.14 MHz, [D$_6$]benzene, 60° C.): δ=6.65 (ps-t, 4H, α-Cp-H), 6.12 (ps-t, 4H, β-Cp-H).

$^{13}$C NMR (100.63 MHz, [D$_6$]benzene, 60° C.): δ=147.7, 145.3 [both m, br, Ph-C(F), C2,2',6,6'], 144.6, 141.8 [both m, br, Ph-C-(F), C4,4'], 139.3, 136.7 [both m, br, Ph-C- (F), C3,3,',5,5'], 128.6, 128.3, 127.0, 121.3 (all d, Cp-C).

$^{11}$B NMR (64.21 MHz, [D$_6$]benzene): δ=54 (91%), −2 (9%).

MS (EI, 70 eV, evaporation temperature 210° C.): m/z (%) =943 (2) [M$^+$ −Cl].

5. Bridged Zirconocene with Boron-Oxygen Bridge by Thermolysis

Preparation of diethoxyboryl (trimethylsilylcyclopentadienyl)-borane

In analogy to the syntheses described, 3.01 g (1.26 mmol, 56%) of product is obtained as a colorless liquid from 3.65 g (24.0 mmol) of chlorodiethoxyborane and 7.23 g (24.0 mmol) of trimethyl (trimethylsilylcyclopentadienyl) tin by reaction at room temperature, followed by distillation.

Main Isomer $^1$H NMR (200.32 MHz, CDCl$_3$): δ=6.55 (br, 4H, Cp-H), 4.04 (q, $^3$J=7 Hz, 4H, CH$_2$), 1.23 (t, 6H, CH$_3$), 0.0 [s, 9H, (CH$_3$)$_3$Si].

Minor Isomers $^1$H NMR (200.32 MHz, CDCl$_3$): δ=7.12, 7.08, 6.94, 6.84 (all m, 1H, Cp-H), 3.22 (m, 1H, allyl-Cp-H), 3.10 (m, 1H, allyl-Cp-H), 0.15 [s, 9H, (CH$_3$)$_3$Si].

All Isomers $^{13}$C NMR (50.13 MHz, CDCl$_3$): δ=148.5, 147.6, 144.9, 144.0, 141.7 (all Cp-C), 138, 132 (both br quart., Cp-C), 59.7, 58.8 (both CH$_2$), 17.5, 17.2 (both CH$_3$), –0.8, –1.2, –1.7 [all (CH$_3$)$_3$Si].

$^{11}$B NMR (64.21 MHz, CDCl$_3$) δ=27.

Preparation of bis [η$^5$-diethoxyborylcyclopentadienyl]dichlorozirconium (IV)

To a suspension of 0.814 g (3.49 mmol) of zirconium tetrachloride in 30 ml of toluene is added a solution of diethoxy(trimethylsilylcyclopentadienyl)borane at once at room temperature. The mixture is heated to 60° C.; after 2 h, an almost clear pale green solution has formed. To complete the reaction, the mixture is allowed to cool to room temperature, and stirring is continued over night. This is followed by filtering, highly concentrating, adding 20 ml of hexane and cooling to –30° C. Colorless needles precipitate which turn out to be practically pure by analysis. The mother liquor is evaporated to dryness, and the grey-green residue is recrystallized from pentane.

Overall yield: 1.44 g (2.93 mmol, 84%), colorless needles which change to green upon contact with air.

$^1$H NMR (200.13 MHz, [D$_6$]benzene): δ=6.87 (ps-t, 4H, α-Cp-H), 6.36 (ps-t, 4H, β-Cp-H), 4.04 (q, $^3$J=7 Hz, 8H, CH$_2$—CH$_3$), 1.15 (t, $^3$J=7 Hz, 12 H, CH$_3$—CH$_2$).

$^{13}$C NMR (50.32 MHz, [D$_6$]benzene): δ=124.6 (d, $^1$J$_{C,H}$=174 Hz, α-Cp-C), 119.5 (d, $^1$J$_{C,H}$=174 Hz, β-Cp-C), 60.1 (t, $^1$J$_{C,H}$=143 Hz, CH$_2$), 17.4 (q, $^1$J$_{C,H}$=126 Hz, CH$_3$).

$^{11}$B NMR (64.21 MHz, [D$_6$]benzene): δ=25.

MS (70 eV, evaporation temperature 140° C.), m/z (%): 490 (8) [M$^+$].

Preparation of oxabis[(ethoxy) boryloxycyclopentadienyl]dichlorozirconium(IV)

A colorless solution of 0.402 g (0.817 mmol) of bis [η$^5$-diethoxyborylcyclopentadienyl]dichlorozirconium(IV) in 25 ml of hexane is refluxed for 2 h. No visually detectable change is observed. After removing the solvent, a colorless precipitate remains which may be recrystallized from hexane.

Yield: 0.304 g (0.529 mmol, 89%), colorless crystalline solid.

$^1$H NMR (200.13 MHz, [D$_6$]benzene): δ=6.61 (ps-t, 4H, α-Cp-H), 6.07 (ps-t, 4H, β-Cp-H), 3.83 (q, $^3$J=7 Hz, 4H, CH$_2$—CH$_3$), 1.06 (t, $^3$J=7 Hz, 6H, CH$_3$—CH$_2$).

$^{13}$C NMR (50.32 MHz, [D$_6$]benzene): δ=126.7 (d, α-Cp-C), 117.8 (d, β-Cp-C), 60.0 (t, CH$_2$), 17.2 (q, CH$_3$).

MS (EI, 70 eV, evaporation temperature 105° C.): m/z (%) =418 (82) [M$^+$].

6. Zirconocene with a One-Membered Boron Bridge

Preparation of bis(trimethylsilylcyclopentadienyl) (phenyl)-borane

To 2.230 g (7.41 mmol) of (trimethylsilylcyclopentadienyl)-trimethyltin is added 0.59 g (0.48 ml, 3.7 mmol) of dichloro-(phenyl)borane dropwise at room temperature. An intense yellow color immediately appears. The mixture is heated at 40° C. for 2 h whereupon the yellow color intensifies. This is followed by fractional distillation wherein the chlorotrimethylstannane formed can first be separated off. In the distillation, a heavy decomposition occurs from about 120° C. bath temperature to give a dark-red oil.

Yield: 0.975 g (2.69 mmol, 73%), yellow liquid, b.p. 100° C./ 10$^{-3}$ mbar.

$^1$H NMR (200.13 MHz, [D$_6$]benzene): δ=8.07 (m, 1H), 7.8 (m, br, 4H, Cp-H), 7.29 (m, 6H, Ph-H), 7.22 (m), 7.05 (m, 1H, Cp-H), 6.98 (m, 1H, Cp-H), 6.76 (m, 1H, Cp-H), 6.72 (m, 1H, Cp-H), 6.7 (m, br, 4H, Cp-H), 3.51 (m, 1H, allyl-Cp-H), 0.15 [s, 9H, (CH$_3$)$_3$Si vinylic, minor isomers], –0.15 [s, 18H, (CH$_3$)$_3$Si allylic, main isomers].

$^{13}$C NMR (50.32 MHz, [D$_6$]benzene): δ=152.9 (Cp-C), 143.2 (Cp-C), 138.0, 137.1 (Ph-C), 136.7, 136.2, 132.6, 132.1 (br), 130.3 (br), 129.9, 127.6 (Ph-C), 51.2 (CH$_2$), –0.8 [(CH$_3$)$_3$Si, minor isomers], –1.4 [(CH$_3$)$_3$Si, main isomer].

MS (EI, 70 eV, evaporation temperature 80° C.): m/z (%) =362 (32) [M$^+$].

Preparation of phenylborylbis[cyclopentadienyl] dichlorozirconium(IV)

To a solution of 0.751 g (2.07 mmol) of bis (trimethylsilylcyclopentadienyl)(phenyl)borane in 250 ml of toluene is added a suspension of 0.390 g (1.67 mmol) of zirconium tetrachloride in 50 ml of toluene incrementally at room temperature. After 5 h at room temperature, the mixture is filtered and freed from solvent in vacuo. By extracting the yellow residue with hot hexane/toluene (20:1), a yellow solution is obtained from which a colorless solid can be obtained by crystallization after concentrating.

Yield: 0.027 g (7%).

$^1$H NMR (200.32 MHz, [D$_6$]benzene): 7.90 (m, 2H, o-Ph-H), 7.28 (m, br, 5H, Ph-H), 6.63 (m, 4H, α-Cp-H), 6.04 (m, 4H, β-Cp-H).

$^{13}$C NMR (50.32 MHz, [D$_6$]benzene): δ=137.3, 136.9, 136.3 (all Ph-C), 119. 3 (Cp-C).

$^{11}$B NMR (64.21 MHz, [D6]benzene): δ=44.

MS (EI, 70 eV, evaporation temperature: 150° C.): m/z (%) =378 (41) [M$^+$].

In an absolutely analogous way, bridged zirconocenes with alkyl, perfluoroalkyl and perfluoroacyl substituents at the boron are synthesized.

7. Zirconocene with a One-Membered Boron Bridge with Indenyl Ligands, Prepared by Deprotonation of the Ligands

Preparation of bis(indenyl) (phenyl)borane

In 50 ml of diethyl ether, 5.01 g (31.5 mmol) of dichloro (phenyl)borane is cooled to –78° C. and a solution of 7.70 g (63.1 mmol) of indenyllithium in 50 ml of diethyl ether is added dropwise within one hour. After warming to room temperature, the mixture is filtered, and the slightly yellow filtrate is highly concentrated in vacuo. Gradual cooling from 0° C. to −20° C. results in the formation of 7.45 g (74%) of bis(indenyl) (phenyl)borane in the form of colorless crystals.

The reaction produces two double-bond isomers (meso+ rac) in a ratio of 1:1, assignment of the $^1$H NMR signals to the individual isomers being impossible.

$^1$H NMR (200.1 MHz, CD$_2$Cl$_2$): δ=7.62–7.19 (m, 26H, Ph, 4-H to 7-H), 7.12 (ddd, 2H, 3-H$_A$ or 3-H$_B$, $^4$J(H4/H3) =0.6 Hz, $^3$J(H2/H3) =5.3 Hz, $^4$J(H1/H3) =2.1 Hz); 6.97 (2 ×Pt, 2H, 3-H$_A$ or 3-H$_B$); 6.71 (dd, 2H, 2-H$_A$ or 2-H$_B$, $^3$J(H3/H2)=5.3 Hz, $^3$J(H1/H2)=1.9 Hz); 6.49 (dd, 2H, 2-H$_A$ or 2-H$_B$, $^3$J(H3/H2) =5. 3 Hz, $^3$J(H1/H2)=1.9 Hz); 4.11, 4.10 ppm (2×bs, 4H, 1-H$_A$ and 1-H$_B$).

In the $^{13}$C NMR, strong superposition of the aromatic resonance signals occurs so that an exact assignment is not possible.

$^{13}$C NMR (50.3 MHz, CD$_2$Cl$_2$): δ=147.1, 146.7, 146.6, 145.8, 137.4, 13 6.1, 135.2, 134.9, 133.2, 133.1, 133.0, 132.8, 128.3, 128.2, 126.5, 126.3, 124.9 (double int.), 124.8, 124.6, 121.85, 121.81, 52.01 ppm (broad).

$^{11}$B NMR (64.21 MHz, CD$_2$Cl$_2$): δ=72.6 ppm.

Preparation of [bis(indenyl)(phenyl)borane] dilithium

A solution of 4.50 g (14.1 mmol) of bis(indenyl) (phenyl) borane in 50 ml of diethyl ether is cooled down to −78° C., and 4.73 g (28.3 mmol) of lithium bis(trimethylsilyl)amide, dissolved in 50 ml of diethyl ether and also cooled at −78° C., is slowly added. The mixture is allowed to reach room temperature in the cooling bath, and after 24 hours, an orange-colored suspension is obtained which is concentrated to dryness in an oil-pump vacuum. After adding 50 ml of pentane, the yellow suspension is suction-filtered, the residue is repeatedly washed with pentane and dried in vacuo, whereby 4.51 g (98%) of the dilithium salt can be isolated as a beige-colored powder.

$^1$H NMR (200.1 MHz, [D$_8$]THF): δ=7.55, 7.25–7.05 (2×m, 11H); 6.37, 6.20 (2 ×pt, 4H); 6.13 ppm (pd, 2H).

Preparation of [phenylborylbis(indenyl)] dichlorozirconium(IV)

A suspension of 4.02 g (12.2 mmol) of [bis(indenyl) (phenyl)-borane]dilithium in 150 ml of toluene and 30 ml of diethyl ether is cooled down to −78° C., and 2.85 g (12.2 mmol) of zirconium tetrachloride is added. The mixture is allowed to warm to room temperature in the cooling bath; after 30 hours, a brown-red suspension is obtained. After filtering off the insolubles, the dark-red filtrate is stored at −20° C. for three days whereupon 908 mg (14%) of an orange-red powder can be isolated. The residual solution is concentrated to dryness in an oil-pump vacuum whereupon 2.45 g of the zirconocene dichloride (contaminated crude product) can be isolated as a red-brown powder.

In the $^1$H NMR of the crude product, strong superposition of the aromatic resonance signals occurs so that an exact assignment is not possible. However, it is clearly evident that one molar equivalent of diethyl ether is coordinated at the boron bridging atom. Further, the two diastereomers are present in a ratio of about 1:1.

$^1$H NMR (200.1 MHz, CD$_2$Cl$_2$): δ=8.13 (m), 7.57–7.46, 7.32–7.07, 6.84 (3×m); 6.80 (dd, 3-H$_A$ or 3 H$_B$, $^3$J(H2/H3)= 3.1 Hz, $^4$J(H4/H3)=0.8 Hz); 6.08 (d, 2-H$_A$ or 2-H$_B$, $^3$J(H3/H2)=3.1 Hz); 6.01 (d, 2-H$_A$ or 2-H$_B$, $^3$J(H3/H2)=3.2 Hz); 4.42 (q, 4H, OCH$_2$CH$_3$, $^3$J=7.1 Hz); 1.34 ppm (t, 6H, OCH$_2$CH$_3$, $^3$J=7.1 Hz).

In the $^1$H NMR of the orange-red powder, only one of the diastereomers can be detected.

$^1$H NMR (200.1 MHz, CD$_2$Cl$_2$): δ=7.95 (m, 2H, o-Ph-H); 7.40 (m, 3H, p- and m-Ph-H); 7.17–6.69 (m, 4H, 4-H to 7-H); 6.66 (dd, 2H, 3-H, $^3$J(H2/H3)=3.2 Hz, $^4$J(H4/H3)=0.9 Hz); 5.87 (d, 2H, 2-H, $^3$J(H3/H2)=3.2 Hz); 4.42 (q, 4H, OCH$_2$CH$_3$, $^3$J=7.1 Hz); 1.34 ppm (t, 6H, OCH$_2$CH$_3$, $^3$J=7.1 Hz).

8. Zirconocene with a One-membered Boron Bridge with Silicon-substituted Cyclopentadienyl Ligands, Prepared by Deprotonation of the Ligands Preparation of bis(trimethylsilylcyclopentadienyl) (phenyl)borane To 4.80 g (30.2 mmol) of dichloro(phenyl)borane, dissolved in 70 ml of diethyl ether, a suspension of 8.36 g (60.4 mmol) of trimethylsilylcyclopentadienyllithium in 100 ml of diethyl ether is slowly added at −78° C. The mixture is allowed to warm to room temperature in the cooling bath, and insolubles are filtered off. After concentrating the yellow filtrate to dryness in an oil-pump vacuum, 10.8 g of bis (trimethylsilylcyclopentadienyl) (phenyl)borane is obtained as a yellow viscous oil.

Due to the dynamic behavior of the trimethylsilyl groups at room temperature, only broad, unassignable signal groups can be seen in the $^1$H NMR.

$^1$H NMR (200.1 MHz, CD$_2$Cl$_2$): δ=7.67, 7.48 (2×m, Ph-H); 7.12, 6.76 (2×bs, Cp-H) ; 0.00 ppm (bs, Me$_3$Si).

$^{11}$B NMR (64.21 MHz, CD$_2$Cl$_2$): δ=ppm.

Preparation of [bis(trimethylsilylcyclopentadienyl) (phenyl)borane]dilithium

To a solution of 8.50 g (23.4 mmol) of bis (trimethylsilylcyclopenadienyl) (phenyl)borane in 70 ml of diethyl ether at −78° C. is slowly added a solution of 7.85 g (46.9 mmol) of lithium bis(trimethylsilyl)amide in 80 ml of diethyl ether, also cooled at −78° C. The mixture is allowed to warm to room temperature in the cooling bath, and after 24 hours, an orange-colored suspension is obtained which is concentrated to dryness in an oil-pump vacuum. After the addition of 50 ml of pentane, the yellow suspension is suction-filtered, the residue is repeatedly washed with pentane and dried in vacuo whereupon 8.53 g (97%) of the dilithium salt can be isolated as a yellow powder.

Preparation of [phenylborylbis (trimethylsilylcyclopentadienyl)]dichlorozirconium (IV)

A suspension of 8.53 g (22.8 mmol) of the dilithium salt in 150 ml of toluene and 50 ml of diethyl ether is cooled down to −78° C., and 5.31 g (22.8 mmol) of zirconium tetrachloride is added. The mixture is allowed to warm to room temperature in the cooling bath, and after 30 hours, an orange-colored suspension is obtained. After filtering off the insolubles, the orange-colored filtrate is concentrated to dryness in an oil-pump vacuum to obtain 12.9 g (95%) of the zirconocene dichloride in the form of a yellow powder as a crude product.

In the $^1$H NMR, both diastereomers (meso and rac) can be detected in a ratio of 1:1. An exact assignment is not possible, however. Further, one molar equivalent of diethyl ether is coordinated at the boron bridge-head atom.

$^1$H NMR (200.1 MHz, CD$_2$Cl$_2$): δ=7.91 (m, 4H, o-Ph-H); 7.46 (m, 6H, m- and p-Ph-H); 6.99 (dd, 2H, Cp-H, $^3$J=2.78 Hz, $^4$J=1.97 Hz); 6.87 (dd, 2H, Cp-H, $^3$J=3.11 Hz, $^4$J=2.95 Hz); 6.13, 5.87, 5.67, 5.61 (4×pt, 2H each, Cp-H), 4.44 (q, 8H, 2×OC$\underline{H}_2$CH$_3$, $^3$J=7.07 Hz); 1.39 (t, 12H, 2×OCH$_2$C$\underline{H}_3$, $^3$J=7.1 Hz); 0.30, 0.29 (2×s, 36H, 2×(CH$_3$)$_3$Si).

11B NMR (64.21 MHz, CD$_2$Cl$_2$): δ=12.7 ppm.

One diastereomer can be significantly accumulated by extraction with pentane:

$^1$H Mpm (200.1 MHz, CD$_2$Cl$_2$): δ=7.91 (m, 2H, o-Ph-H); 7.46 (m, 3H, m- and p-Ph-H); 6.99 (dd, 2H, Cp-H, $^3$J=2.78 Hz, $^4$J=1.97 Hz); 6.13, 5.61 (2×pt, 2H each, Cp-H), 4.44 (q, 4H, OC$\underline{H}_2$CH$_3$, $^3$J=7.07 Hz); 1.39 (t, 6H, OCH$_2$C$\underline{H}_3$, $^3$J=7.1 Hz); 0.3 0 ppm (s, 18H, (CH$_3$)$_3$Si).

9. Zirconocene with a One-membered Boron Bridge with Differently Substituted Cyclopentadienyl Ligands, Prepared by Deprotonation of the ligands Preparation of (chloro) (indenyl) (phenyl)borane In 50 ml of diethyl ether, 3.65 g (23.0 mmol) of dichloro (phenyl)borane is cooled down to −78° C., and a solution of 2.69 g (22.0 mmol) of indenyllithium in 50 ml of diethyl ether is added dropwise within one hour. After warming to room temperature, the LiCl formed is filtered off, and the slightly yellow diethyl ether phase is concentrated to dryness in an oil pump vacuum. 5.14 g (98%) of (chloro) (indenyl) (phenyl)borane is obtained as a yellow oil.

$^1$H NMR (200.1 MHz, CD$_2$Cl$_2$): δ=8.2 (pd, 2H, o-Ph-H); 7.75–6.93 (m, 8H, p- and m-Ph-H, 3-H to 7-H); 6.75 (dd, 1H, 2-H, $^3$J(H3/H2) =5.4 Hz, $^3$J(H1/H2)=1.9 Hz); 4.77 ppm (bs, 1H, 1-H).

Preparation of (cyclopentadienyl)(indenyl)(phenyl) borane

To 2.40 g (10.1 mmol) of (chloro) (indenyl) (phenyl) borane in 20 ml of diethyl ether is slowly added a suspension of 725 mg (10.1 mmol) of lithium cyclopentadienyl in 30 ml of diethyl ether at −78° C. The mixture is allowed to warm to 0° C. in the cooling bath, insolubles are filtered off, and concentrating the filtrate in vacuo yields 2.47 g (91%) of (cyclopentadienyl)(indenyl)(phenyl)borane as a yellow oil.

The formation of numerous double-bond isomers makes an unambiguous spectroscopical assignment impossible. However, especially numerous pseudoquartets in the $^1$H NMR in the range of from 2.8 to 3.7 ppm can be assigned to the allylic cyclopentadienyl protons.

Preparation of [(cyclopentadienyl)(indenyl)(phenyl) borane]dilithium

To a solution of 2.47 g (9.21 mmol) of (cyclopentadienyl) (indenyl)(phenyl)borane in 30 ml of diethyl ether is carefully added a slight suspension of 3.08 g (18.4 mmol) of lithium bis(trimethylsilyl)amide in 20 ml of diethyl ether at −78° C. The mixture is allowed to warm to room temperature in the cooling bath, and after 24 hours, a yellow suspension is obtained which is concentrated to dryness in an oil-pump vacuum. After the addition of 50 ml of pentane, the yellow suspension is suction-filtered, the residue is repeatedly washed with pentane and dried in vacuo whereupon 1.17 g (45%) of the dilithium salt can be isolated as a yellow powder.

Preparation of [phenylboryl(cyclopentadienyl) (indenyl)]dichlorozirconium(IV)

A suspension of 1.17 g (4.18 mmol) of [(cyclopentadienyl)(indenyl)(phenyl)borane]dilithium in 30 ml of toluene and 10 ml of diethyl ether is cooled down to −78° C., and 974 mg (4.18 mmol) of zirconium tetrachloride is added. The mixture is allowed to warm to room temperature in the cooling bath, and after 30 hours, an orange-colored suspension is obtained. After filtering of the insolubles, the orange-colored filtrate is concentrated to dryness in an oil-pump vacuum to obtain 800 mg (38%) of the zirconocene dichloride in the form of a yellow powder as a crude product.

$^1$H NMR (200.1 MHz, CD$_2$Cl$_2$): δ=7.84, 7.73 (2×m, 2H, o-Ph-H); 7.34, 6.67, 6.48 (3×m, 6H, m- and p-Ph-H, 3-H to 4-H); 6.79 (dd, 1H, 3-H, $^3$J=3.20 Hz, $^4$J=1.14 Hz); 5.85 (d, 1H, 2-H, $^3$J=3.20 Hz); 5.58, 5.46 (2×m, 4H, Cp-H), 4.27 (q, 8H, 2×OC$\underline{H}_2$CH$_3$, $^3$J=7.1 Hz); 1.25 ppm (t, 12H, 2×OCH$_2$ C$\underline{H}_3$, $^3$J=7.1 Hz).

$^{11}$B NMR (64.21 MHz, CD$_2$Cl$_2$): δ=11.58 ppm.

10. Silicon-bridged Zirconocene with Phenyl Substituents at the Boron, both Cyclopentadienyl Ligands being Boron-substituted Preparation of bis[(diphenylboryl)cyclopentadienyl] dimethylsilane To a suspension of 2.11 g (10.5 mmol) of bis (cyclopentadienyl)dimethylsilanedilithium in 50 ml of diethyl ether is rather quickly added a solution of 4.19 g (20.9 mmol) of chlorodiphenylborane in 20 ml of diethyl ether dropwise at −60° C. The mixture is allowed to reach room temperature over night, filtered, the colorless precipitate is washed with 20 ml of diethyl ether, and the yellow filtrate is freed from solvent in vacuo. The yellow oily residue is taken up twice in 30 ml of pentane and freed from solvent in vacuo.

Yield: 5.25 g (10.2 mmol, 97%), yellow oil.

A mixture of diastereomers is obtained.

$^1$H NMR (200.13 MHz, [D$_6$]benzene): δ/ppm=−0.35, −0.32, 0.00, 0.04 (all s, Si(CH$_3$)$_2$); 6.5–6.8 (br, Cp-H); 7.0–8.0 (m, Cp-H and Ph-H).

$^{11}$B NMR (64.21 MHz, [D6]benzene): δ/ppm=62.

MS (EI, 70 eV): m/z (%)=516 [M$^+$].

Preparation of bis[(diphenylboryl)cyclopentadienyl] dimethylsilanedilithium

To a solution of 3.79 g (23.5 mmol) of bis(trimethylsilyl) amine in 70 ml of diethyl ether is added 12.5 ml (20.0 mmol)

Yield: 3.43 g (5.07 mmol, 78%), beige-colored powder.

A mixture of diastereomers (rac and meso) is obtained.

$^1$H NMR (300.14 MHz, CD$_2$Cl$_2$): δ=0.12, 0.15 (all s, 6H, Si(CH$_3$)$_2$); 6.28, 6.38 (all m, 4H, Cp-H); 7.0–7.6 (m, 22H, Cp-H and Ph-H).

$^{13}$C NMR (75.48 MHz, CD$_2$Cl$_2$): δ/ppm=1.3, 4.5 (Si (CH$_3$)$_2$); 116.7, 117.7, 118.8, 123.5, 124.3, 127.5, 127.8, 127.9, 129.5, 130.4, 131.3, 131.9, 136.0, 137.6, 137.7, 139.0, 143.3 (Cp-H and Ph-H).

$^{11}$B NMR (64.21 MHz, CD$_2$Cl$_2$): δ/ppm=56.

MS (EI, 70 eV): m/z (%)=676 [M+].

We claim:

1. A method for the preparation of substituted zirconocenes and hafnocenes, characterized in that said zirconocene or hafnocene is obtained from silicon- and tin-substituted cyclopentadienyls by replacing the tin residue by boron by means of haloboranes, followed by replacing the silicon by reaction with zirconium or hafnium halides.

2. The method according to claim 1, characterized in that boranes containing two substituted cyclopentadienyl residues each of which bears at least one silyl residue are reacted with zirconium or hafnium halides for the preparation of bridged zirconocenes and hafnocenes with boron as the bridging atom.

3. The method according to claim 1 and 2, characterized in that diborylated unbridged zirconocenes and hafnocenes are subjected to a mild thermolysis for the preparation of bridged zirconocenes and hafnocenes with two boron atoms and one oxygen atom constituting the bridge.

4. A method for the preparation of substituted zirconocenes and hafnocenes by deprotonating the ligand precursors followed by transmetallation by reaction with zirconium or hafnium halides, characterized in that boron-substituted cyclopentadienyls are deprotonated with weakly nucleophilic bases followed by reaction with zirconium or hafnium halides.

5. The method according to claim 4, characterized in that lithium bis(trimethylsilyl)amide is used as said weakly nucleophilic base.

6. The method according to claim 4, characterized in that boranes containing two substituted cyclopentadienyl residues are deprotonated with weakly nucleophilic bases followed by reaction with zirconium or hafnium halides for the preparation of bridged zirconocenes and hafnocenes with boron as the bridging atom.

7. The method according to claim 6, characterized in that lithium bis(trimethylsilyl)amide is used as said weakly nucleophilic base.

8. Zirconocenes and hafnocenes having the general formula I

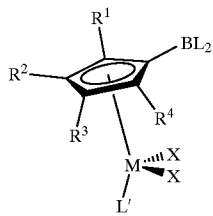

in which M=Zr or Hf, $R^1$–$R^4$, being the same or different, represent H, methyl, ethyl, allyl, phenyl, aryl, benzyl residues and heteroatoms, such as halogens (F, Cl, Br, I), silicon and germanium, wherein the cyclopentadienyl ligand may also be an anellated cyclopentadienyl ligand, such as indenyl, tetrahydroindenyl, which may again bear substituents, such as alkyl, aryl, benzyl residues or heteroatoms, such as halogens (F, Cl, Br, I), silicon and germanium;

L' is another cyclopentadienyl ligand with $R^1$–$R^4$ being as defined above which may also be free of boron, or L'=X;

L represents alkyl, aryl, benzyl, fluorinated alkyl or aryl residues, halogens (F, Cl, Br, I), OH, alkoxy, wherein these residues may be part of a cycle; and X represents a halogen (F, Cl, Br, I) or N.

9. Zirconocenes and hafnocenes having the general formula II

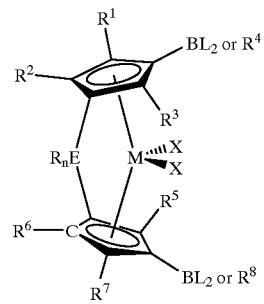

in which M=Zr or Hf, $R^1$–$R^8$, being the same or different, represent H, methyl, ethyl, allyl, phenyl, aryl, benzyl residues and heteroatoms, such as halogens (F, Cl, Br, I), silicon and germanium, with the proviso that at least one of $R^4$ or $R^8$ is $BL_2$, wherein the cyclopentadienyl ligand may also be an anellated cyclopentadienyl ligand, such as indenyl, tetrahydroindenyl, which may again bear substituents, such as alkyl, aryl, benzyl residues or heteroatoms, such as halogens (F, Cl, Br, I), silicon and germanium;

the bridge $R_nE_m$, with n=1 or 2 and m=1, 2 or 3, is composed of the same or different building blocks containing a group with a IVth main group element wherein E represents C, Si and Ge, and R represents H, alkyl, aryl and benzyl, or the bridge $R_nE$ may also contain boron, wherein E=B, n=1, R=H, alkyl, aryl and benzyl, fluorinated alkyl or aryl, alkoxy, OH, halogens (F, Cl, Br, I), alone or in combination with the above mentioned bridging components, or with a VIth main group element, such as oxygen or sulfur;

L represents alkyl, aryl, benzyl, fluorinated alkyl or aryl residues, halogens (F, Cl, Br, I), OH, alkoxy, wherein these residues may be part of a cycle; and X represents a halogen (F, Cl, Br, I) or N.

10. Compound of claim 8, being Bis [$\eta^5$-diethylborylcyclopentadienyl]dichlorozirconium (IV).

11. Compound of claim 8, being ($\eta^5$-(3-Methyl-2,3-dihydrobenzoboroyl)cyclopentadienyl) ($\eta^5$-cyclopentadienyl)dichlorozirconium (IV).

12. Compound of claim 8, being ($\eta^5$-2,3-Dioxabenzoboroylcyclopentadienyl) ($\eta^5$-cyclopentadienyl) dichlorozirconium (IV).

13. Compound of claim 8, being Bis [$\eta^5$-bis (pentafluorophenyl)borylcyclopentadienyl] dichlorozirconium (IV).

14. Compound of claim 8, being Bis [$\eta^5$-diethoxyborylcyclopentadienyl]dichlorozirconium (IV).

15. Compound of claim 9, being Oxabis [(ethoxy) boryloxycyclopentadienyl]dichlorozirconium (IV).

16. Compound of claim 9, being Phenylborylbis [cyclopentadienyl]dichlorozirconium (IV).

* * * * *